(12) United States Patent  
Lucciulli et al.

(10) Patent No.: US 9,724,681 B2  
(45) Date of Patent: Aug. 8, 2017

(54) MODIFYING ORGANOALUMINUM CO-CATALYSTS FOR IMPROVED PERFORMANCE

(71) Applicant: SABIC GLOBAL TECHNOLOGIES B.V., Riyadh (SA)

(72) Inventors: Sebastiano Lucciulli, Riyadh (SA); Roland Schmidt, Wiehl (DE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/115,711

(22) PCT Filed: Feb. 4, 2015

(86) PCT No.: PCT/IB2015/050844  
§ 371 (c)(1),  
(2) Date: Aug. 1, 2016

(87) PCT Pub. No.: WO2015/118462  
PCT Pub. Date: Aug. 13, 2015

(65) Prior Publication Data  
US 2017/0007994 A1     Jan. 12, 2017

Related U.S. Application Data

(60) Provisional application No. 61/936,631, filed on Feb. 6, 2014.

(51) Int. Cl.  
*C08F 2/00*     (2006.01)  
*C08F 4/00*     (2006.01)  
(Continued)

(52) U.S. Cl.  
CPC ......... *B01J 31/143* (2013.01); *B01J 31/0204* (2013.01); *B01J 31/0212* (2013.01);  
(Continued)

(58) Field of Classification Search  
CPC .. B01J 31/143; B01J 31/0204; B01J 31/0212; B01J 35/0006; B01J 37/04;  
(Continued)

(56) References Cited

U.S. PATENT DOCUMENTS

| | | | | |
|---|---|---|---|---|
| 4,615,998 A | * | 10/1986 | Le Quan | B01J 31/0212 502/126 |
| 6,153,550 A | * | 11/2000 | Kissin | B01J 31/143 502/103 |
| 2008/0058534 A1 | * | 3/2008 | Knudsen | B01J 31/0244 548/402 |

FOREIGN PATENT DOCUMENTS

| EP | 0221206 | * | 5/1987 |
|---|---|---|---|
| EP | 0221206 A1 | | 5/1987 |

(Continued)

OTHER PUBLICATIONS

Forestiere, A., et al., "Oligomerization of Monoolefins by Homogeneous Catalysts", Oil & Gas Science and Technology—Rev. IFP, (2009) 64(6):649-667.

(Continued)

*Primary Examiner* — William Cheung  
(74) *Attorney, Agent, or Firm* — Cantor Colburn LLP (57) ABSTRACT

Processes of making catalyst compositions are provided. In an exemplary embodiment, the processes include modifying an organoaluminum compound with a modifier that decreases the initial reducing strength of the organoaluminum compound, where the modifier can be an ether, an anhydride, an amine, an amide, a silicate, a silyl ether, a siloxane, an ester, a carbonate, a urea, a carbamate, a sulfoxide, a sulfone, a phosphoramide, or a combination thereof. The processes further include adding a transition metal complex to the mixture of the organoaluminum com- (Continued)

pound and the modifier; and obtaining a catalyst composition including the organoaluminum compound and the transition metal complex.

19 Claims, 1 Drawing Sheet (51) Int. Cl.
B01J 31/14 (2006.01)
B01J 31/02 (2006.01)
B01J 35/00 (2006.01)
B01J 37/04 (2006.01)
C07C 2/34 (2006.01)
C08F 110/08 (2006.01)

(52) U.S. Cl.
CPC ........... *B01J 35/0006* (2013.01); *B01J 37/04* (2013.01); *C07C 2/34* (2013.01); *C08F 110/08* (2013.01); *B01J 2231/10* (2013.01); *B01J 2231/20* (2013.01); *B01J 2531/007* (2013.01); *C07C 2531/14* (2013.01)

(58) Field of Classification Search
CPC ................ B01J 2231/10; B01J 2231/20; B01J 2531/007; C07C 2/34; C07C 2531/007; C08F 10/08
USPC ...................................... 526/75, 90
See application file for complete search history.

(56) References Cited

FOREIGN PATENT DOCUMENTS

EP 2070593 * 6/2009
EP 2070593 A1 6/2009

OTHER PUBLICATIONS

International Search Report of International Application No. PCT/IB2015/050844 mailed Apr. 28, 2015, 5 pages.
Written Opinion of International Searching Authority for International Application No. PCT/IB2015/050844 mailed Apr. 28, 2015, 6 pages.
Ziegler, Karl, "Aluminium-organische Synthese im Bereich olefinischer Kohlenwasserstoffe", Angewandte Chemie (1952) 64:12, pp. 323-329.

* cited by examiner

MODIFYING ORGANOALUMINUM CO-CATALYSTS FOR IMPROVED PERFORMANCE

This application is a national stage application of PCT/IB2015/050844 filed Feb. 4, 2015, which claims priority to U.S. Provisional Patent Application 61/936,631 filed Feb. 6, 2014, both of which are hereby incorporated by reference in their entirety.

FIELD

The presently disclosed subject matter relates to methods of modifying organoaluminum co-catalysts and of making catalyst compositions used in olefin oligomerization processes and other processes.

BACKGROUND

Various catalytic processes involve co-catalysts based on organoaluminum compounds such as TEAL (triethylaluminum), EASC (ethylaluminum sesquichloride), and others. Such co-catalysts may be used in conjunction with other catalysts, e.g., transition metal complexes, to perform various catalytic processes and promote various chemical reactions. Organoaluminum co-catalysts are used in particular for olefin oligomerization processes. For example, organoaluminum co-catalysts can be used in conjunction with transition metal complexes to produce catalyst compositions capable of oligomerizing ethylene (ethene) to 1-butene. Organoaluminum co-catalysts are also used in various olefin polymerization processes. For example, organoaluminum co-catalysts can be used in conjunction with transition metal complexes to produce catalyst compositions capable of generating polyethylene, polypropylene, and other polymers.

1-Butene has for a long time been a desirable substance in the chemical industry. Not only can 1-butene be converted to polybutene-1 and butylene oxides, it can also be used as a co-monomer with ethylene for the production of high strength and high stress crack resistant polyethylene resins. The major industrial routes for producing 1-butene include steam cracking of $C_4$ hydrocarbon streams, ethylene oligomerization processes, refinery operations of crude oil, and ethylene dimerization processes. Catalytic dimerization of ethylene into 1-butene produces higher chain polymers via the growth reaction of the organoaluminum compounds (Ziegler, Angew. Chem. (1952); 64:323-329; J. Boor, Editor, Ziegler-Natta Catalysts and Polymerizations, Acad. Press (New York) 1979; Handbook of Transition Metal Polymerization Catalysts, R. Hoff, R. T. Mathers, Eds. 2010 John Wiley & Sons).

One route to the preparation of 1-butene is the cracking of higher petrochemical fractions containing more than four carbon atoms. A further route to the preparation of 1-butene is via the catalytic dimerization of ethylene. The industrial synthesis of 1-butene can be achieved using nickel or titanium catalysts in large industrial processes such as Alphabutol™ (Handbook of Petroleum Processing, Edited by D. S. J. Jones, P. R. Pujadó; Springer Science 2008; Forestière et al., Oil & Gas Science and Technology-Rev. IFP (2009); 64(6):649-667).

In the Alphabutol™ system and other existing processes for preparation of 1-butene by catalytic dimerization of ethylene, catalyst compositions are formed by combining organoaluminum co-catalysts with transition metal complexes. For example, a solution of an organoaluminum co-catalyst in a hydrocarbon solvent can be mixed with a solution of a titanium complex in an ether solvent to obtain a catalyst composition, which is used to prepare 1-butene, as in the Alphabutol™ system. Such catalyst systems can suffer from drawbacks, which include low catalyst activity, a lengthy induction period, and process fouling, including precipitation of polyethylene. The catalytic activity of the Alphabutol™ system can be relatively low at roughly 1 kg of product per gram of titanium. Polymer formation and lengthy initial induction period are major drawbacks for the commercial Alphabutol™ system.

There remains a need in the art for an organoaluminum co-catalyst composition that is suitable for various processes, including dimerization of ethylene, and is characterized by one or more of improved catalytic activity, shortened induction period, long lifetimes, and high selectivity.

SUMMARY

The presently disclosed subject matter provides processes of making catalyst compositions. In some embodiments, a non-limiting exemplary process includes modifying an organoaluminum compound with a modifier that decreases the initial reducing strength of the organoaluminum compound. The modifier can be an ether, an anhydride, an amine, an amide, a silicate, a silyl ether, a siloxane, an ester, a carbonate, a urea, a carbamate, a sulfoxide, a sulfone, a phosphoramide, an acetal, or a combination thereof. The process further includes adding a transition metal complex to the mixture of the organoaluminum compound and the modifier, and obtaining a catalyst composition including the organoaluminum compound and the transition metal complex.

In certain embodiments, the transition metal complex can include at least one of the metals of Groups IV-B, V-B, VI-B, and VIII of the Periodic Table. The metal(s) can be titanium, zirconium, hafnium, vanadium, niobium, tantalum, chromium, molybdenum, tungsten, iron, cobalt, nickel, or a combination thereof. In some embodiments, the transition metal complex is titanium tetra-n-butoxide.

In certain embodiments, the organoaluminum compound can be triethylaluminum.

In certain embodiments, the modifier is an ether. The ether can be a monoether. In some embodiments, the monoether is tetrahydrofuran. In another embodiment, the ether includes at least two ether groups. In some embodiments, the ether is 1,2-dimethyl ethylene glycol ether. In another embodiment, the ether is a dioxane, which can be 1,4-dioxane.

In certain embodiments, the transition metal complex is not mixed with a catalyst modifier prior to adding the transition metal complex to the mixture of the organoaluminum compound and the modifier.

In some embodiments, the transition metal complex is diluted in a solvent, which can be an alkane, an aromatic hydrocarbon, an olefin, or a combination thereof.

In certain embodiments, the catalyst compositions are suitable for catalytic dimerization of ethylene (ethene). In certain embodiments, the catalyst composition is suitable for producing 1-butene.

In some embodiments, the molar ratio of the organoaluminum compound to the modifier is about 1:5.

In certain embodiments, the process can further include cooling the mixture of the organoaluminum compound and the modifier to ambient conditions prior to adding the transition metal complex to the mixture.

The presently disclosed subject matter also provides catalyst compositions made by the above-described processes.

The catalyst compositions can be used for catalytic dimerization of ethylene, among other reactions. Furthermore, the presently disclosed subject matter provides processes for preparing α-olefins, which include providing the above-described catalyst composition, and contacting an alkene with the catalyst composition to obtain the α-olefins. The α-olefins can include 1-butene. In addition, the presently disclosed subject matter provides processes for preparing a polymer, which can include providing the above-described catalyst composition, and contacting an alkene with the catalyst composition to obtain the polymer. In these processes for preparing α-olefins and processes for preparing a polymer, the alkene can be ethylene, and the alkene and the catalyst composition can come into contact in a homogeneous liquid phase. In one example, the alkene and the catalyst composition can come into contact in a liquid phase, which includes at least about 50 wt. % 1-butene, based on the total weight of the liquid phase. These processes can be conducted at a pressure of from about 1 bars to about 250 bars. These processes can be conducted at a temperature of from about 40° C. to about 150° C. These processes can be conducted in a homogeneous liquid phase. Additionally, the presently disclosed subject matter provides processes for preparing a downstream product, which includes preparing α-olefins by the above-described process, and reacting the α-olefins to obtain the downstream product. The downstream product can be a polymer, which can be a poly-α-olefin or copolymer including at least an α-olefin as a co-monomer. The downstream product can be converted into a shaped body.

DETAILED DESCRIPTION

The presently disclosed subject matter provides processes of making catalyst compositions. The disclosed catalyst compositions can be used for various purposes, e.g., catalytic dimerization of ethylene (ethene) to produce 1-butene.

The catalyst compositions include a transition metal complex and an organoaluminum compound. In the catalyst composition, the transition metal complex can be the main catalyst, and the organoaluminum compound can be a co-catalyst or an activator to activate the transition metal complex. The organoaluminum compound can activate the transition metal complex via reduction reactions, i.e., the organoaluminum compound can be a reducing agent for the transition metal complex. For example, the organoaluminum compound can transfer electrons to the metal center of the transition metal complex. The transition metal complex can be reduced by the organoaluminum compound to various oxidation states. Some of the reduced transition metal complexes are beneficial and some are not, depending on the nature of the chemical reaction being catalyzed. The organoaluminum compound may also act as a co-catalyst or an activator of the transition metal complex by releasing free coordination sites on the metal center of the transition metal complex and/or by exchanging ligands with the transition metal complex to generate organotransition metal bonds.

As noted above, a transition metal complex can be the main catalyst in a catalyst composition that further includes an organoaluminum compound as co-catalyst. The transition metal complex can include at least one of the metals of Groups IV-B, V-B, VI-B, and VIII of the Periodic Table. The suitable metals include, but are not limited to, titanium, zirconium, hafnium, vanadium, niobium, tantalum, chromium, molybdenum, tungsten, iron, cobalt, nickel, and a combination thereof. The transition metal complex can be an alkyl titanate having a general formula $Ti(OR)_4$, where R is a linear or branched alkyl radical having from about 1 to about 12 carbon atoms, e.g., a $C_2$-$C_{12}$ alkyl group, a $C_2$-$C_8$ alkyl group, or a $C_3$-$C_5$ alkyl group. In some embodiments, the alkyl group is isopropyl or butyl, preferably n-butyl. In certain embodiments, the transition metal complexes include titanium. Suitable transition metal complexes including titanium include, but are not limited to, tetraethyl titanate, tetraisopropyl titanate, titanium tetra-n-butoxide (TNBT), and tetra-2-ethyl-hexyl titanate. In some embodiments, the transition metal complex is titanium tetra-n-butoxide.

The transition metal complex can be present in high concentration in the catalyst composition. In some embodiments, the transition metal complex is present in a concentration of from about 0.0001 to about 0.1 mol/dm$^3$, from about 0.0001 to about 0.0005 mol/dm$^3$, from about 0.0005 to about 0.001 mol/dm$^3$, from about 0.001 to about 0.01 mol/dm$^3$, from about 0.01 to about 0.1 mol/dm$^3$.

In certain embodiments, the transition metal complex can be diluted or dissolved in a solvent, which includes, but is not limited to, alkanes (including $C_2$-$C_{12}$ alkanes or $C_4$-$C_8$ alkanes, e.g., pentane, hexane, heptane, octane), aromatic hydrocarbons (benzene, toluene), and olefins or alkenes (including $C_2$-$C_{12}$ alkenes or $C_4$-$C_8$, e.g., 1-butene, pentenes, hexenes). In some embodiments, the transition metal complex is diluted in n-hexane. In other embodiments of the presently disclosed subject matter, the transition metal complex can be first mixed or reacted with a modifier, which can be an ether (e.g., diethyl ether, THF, or 1,4-dioxane) or another polar additive capable of coordinating to the transition metal.

The organoaluminum compound can be a co-catalyst or an activator to activate a transition metal complex in a catalyst composition. The organoaluminum compound can have the general formula of $Al(R)_3$, where R can be a hydrocarbon, H or a halogen, or mixtures thereof. Each R in a molecule may be the same as or different to the other R groups in the molecule. Organoaluminum compounds are known to one of ordinary skill in the art and the artisan can select the organoaluminum compounds in order to enhance the advantageous properties of the process according to the presently disclosed subject matter. In some embodiments, R is an alkyl group. R can be a straight chain or branched chain alkyl group. In some embodiments, R is a straight chain alkyl group. R can be a $C_1$-$C_{12}$ alkyl group, a $C_1$-$C_8$ alkyl group, or a $C_1$-$C_4$ alkyl group. In some embodiments, the alkyl group is ethyl. Suitable organoaluminum compounds include, but are not limited to, triethylaluminum (TEAL), trimethylaluminum (TMA), tripropylaluminum, triisobutylaluminum, diisobutylaluminum hydride, ethylaluminum sesquichloride (EASC), and trihexylaluminum. In some embodiments, the organoaluminum compound is aluminum trialkyls, which can be triethylaluminum and trimethylaluminum. Aluminum trialkyls exist in both dimeric form and monomeric form.

Figure 1:
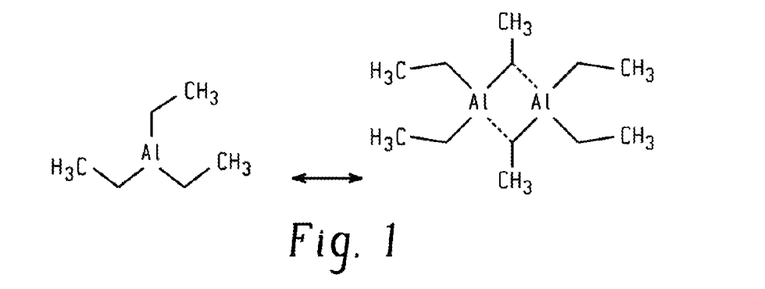
FIG. 1 represents the dimeric and monomeric forms of triethylaluminum.

In some embodiments, the organoaluminum compound is TEAL. TEAL is a volatile, colorless, and highly pyrophoric liquid. TEAL can be stored in hydrocarbon solvents such as hexane, heptane, or toluene. TEAL exists in dimeric form as $Al_2Et_6$ and monomeric form as $AlEt_3$, where Et is an ethyl ($CH_2CH_3$) group (see FIG. 1). One pair of ethyl groups is bridging and four ethyl groups are terminal ligands as shown in FIG. 1. At higher temperatures, the dimer $Al_2Et_6$ cracks into the monomer $AlEt_3$.

In another embodiment, the organoaluminum compound is TMA. Similar to TEAL, TMA is a pyrophoric and colorless liquid. TMA also exists in dimeric form as $Al_2Me_6$ and monomeric form as $AlMe_3$, where Me is a methyl ($CH_3$) group. TMA exists mostly as a dimer at ambient temperature and pressure. The shared methyl groups bridge between the two aluminum atoms (3-centered-2-electron bonds) tend to undergo reactions with Lewis bases that would give products consisting of 2-centered-2-electron bonds. For instance, $R_3N$—$AlMe_3$ can be obtained upon treating the TMA dimer with amines. $(AlMe_2Cl)_2$ can be obtained upon treating a TMA dimer with aluminum trichloride. TMA monomer $AlMe_3$, which has an aluminum atom bonded to three methyl groups, usually exists at high temperature and low pressure.

The processes of the presently disclosed subject matter include modifying with a modifier the organoaluminum compound useful as a co-catalyst. The modifier can be a chemical species that modifies the initial reducing strength of the organoaluminum compound, i.e., a reduction modifier. The reducing strength of a given organoaluminum compound can be an important factor in the behavior of a catalyst system comprising an organoaluminum compound and a transition metal complex, as the organoaluminum compound can activate the transition metal complex by reduction to form catalytically active species. For example, an organoaluminum compound can activate an alkyl titanate to generate a catalyst composition to produce 1-butene from catalytic dimerization of ethylene. However, due to the strong reducing strength of the organoaluminum compound, it can deactivate the activated transition metal complex via further reduction reactions. The activated transition metal complex can be deactivated to various inactive species, including, but not limited to, various mixed oxidation state complexes of the transition metal and aluminum. Without being bound to any particular theory, it is possible that, for example, titanium complexes can be deactivated when reduced to low oxidation states including Ti(I) and Ti(II), which are relatively ineffective as catalysts.

Figure 2:
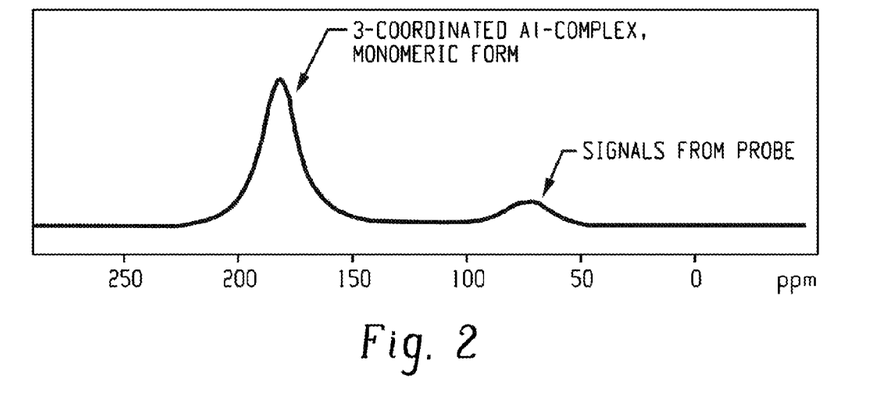
FIG. 2 represents the NMR spectral data of an organoaluminum compound in presence of a modifier.

In the presence of the modifier, the organoaluminum compound primarily exists in monomeric form. The organoaluminum compound monomer can coordinate to the modifier, as shown in FIG. 2. As shown in FIG. 2, in the presence of the modifier, e.g., THF, the polarity of the solvent around the organoaluminum compound increases. The increased polarity of the solvent results in a significant shift of Al NMR signal to a lower field, i.e., a higher chemical shift (56.0 ppm to 183.0 ppm), which indicates the formation of monomeric form of TMA. The modifier can lower or decrease the initial reducing strength of the organoaluminum compound ("taming" it), thereby discouraging over-reduction of the transition metal complex to inactivated species and/or discouraging the deactivation of the activated transition metal complex.

The catalyst composition can be used for catalytic dimerization of ethylene, e.g., to produce 1-butene. Modifying the organoaluminum compound with the modifier prior to mixing the organoaluminum compound with the transition metal complex can improve the overall catalytic activity of the transition metal complex. In the commercial Alphabutol™ system, the main catalyst is TNBT and the co-catalyst is TEAL. The catalytic activity of the transition metal complex of the presently disclosed catalyst composition can be at least about 30% greater, at least about 40% greater, at least about 50% greater, at least about 60% greater, at least about 70% greater, at least about 80% greater, at least about 90% greater, at least about 100% greater, at least about 105% greater, at least about 108% greater, at least about 110% greater, at least about 120% greater, at least about 130% greater, at least about 140% greater, or at least about 150% greater than the catalytic activity of TNBT in the commercial Alphabutol™ system. In some embodiments, the catalytic activity of the transition metal complex of the presently disclosed catalyst composition is from about 40% greater to about 100% greater (e.g., about 48% greater, about 60% greater, or about 97% greater) than the catalytic activity of the TNBT in the commercial Alphabutol™ system. The catalytic activity can be measured or evaluated based on the total ethylene consumption in the catalytic dimerization of ethylene by using a catalyst composition, e.g., the presently disclosed catalyst composition or the commercial Alphabutol™ system.

In the commercial Alphabutol™ system, the main catalyst TNBT is first mixed or reacted with a catalyst modifier. TEAL can then be added to activate TNBT. Catalyst modifiers can be polar additives and can coordinate to TNBT with a pair of electrons, thereby effecting changes in the nature of active metal centers and having a profound effect on the catalyst activity and selectivity. The catalyst modifier can be an ether, e.g., THF. In one example of the presently disclosed catalyst composition, the transition metal complex is not mixed with and is free of a catalyst modifier (e.g., THF). In this example, the transition metal complex is instead diluted in a solvent, which includes, but is not limited to, alkanes (including $C_2$-$C_{12}$ alkanes or $C_4$-$C_8$ alkanes, e.g., pentane, hexane, heptane, octane), aromatic hydrocarbons (benzene, toluene), and olefins or alkenes (including $C_2$-$C_{12}$ alkenes or $C_4$-$C_8$, e.g., 1-butene, pentenes, hexenes). In some embodiments, the transition metal complex is diluted in n-hexane.

The modifier can be various compounds capable of modifying an organoaluminum compound. For example, the modifier can be an aprotic compound possessing lone pair electrons capable of coordinating to an organoaluminum compound. The modifier can be a compound that decreases the initial reducing strength of an organoaluminum compound. The reaction modifier can be an ether, an anhydride, an amine, an amide, a silane, a silicate, a silyl ether, a siloxane, an ester, a carbonate, a urea, a carbamate, a sulfoxide, a sulfone, a phosphoramide, an acetal, or a combination thereof.

In some embodiments, the modifier is an ether. The ether can be a monoether or a polyether including at least two ether groups. The monoethers and polyethers can be symmetrical or unsymmetrical. Substituents of the ethers can be alkyl, cycloalkyl, cycloalkylene (wherein two substituents are joined and the ether oxygen is a ring member), aryl, or other groups having a total of 16 carbon atoms, for example $C_1$-$C_6$ alkyl, $C_3$-$C_6$ cycloalkyl, $C_3$-$C_6$cycloalkylene, $C_{6-10}$ aryl, or $C_2$-$C_6$ alkenyl groups optionally substituted with 1, 2, or 3 substituents selected from halogen, cyano, nitro, $C_1$-$C_3$ alkyl, phenyl, or $C_2$-$C_6$ alkenyl. Suitable alkylene groups can be butylene and pentylene, and suitable alkyl groups can be methyl, ethyl, propyl, n-butyl, iso-butyl, t-butyl, and other higher alkyl groups. In some embodiments, the ether is a monoether. Suitable monoethers include, but are not limited to, diethyl ether, dipropyl ether, dibutyl ether, methyl ethyl ether, methyl propyl ether, methyl butyl ether, methyl tert-butyl ether, ethyl propyl ether, ethyl butyl ether, propyl butyl ether, tetrahydrofuran (THF), and dihydropyran. In some embodiments, the monoether is THF.

In another embodiment, the ether is a polyether that includes at least two ether groups. Such polyethers include cyclic diethers, in particular a substituted or unsubstituted cyclic diether having a total of 3 to 14 carbon atoms, or 4 to 10 carbon atoms, or 4 to 8 carbon atoms. Cyclic diethers can be dioxanes, including, but not limited to, 1,4-dioxane, or a 1,4-dioxane optionally substituted with 1, 2, or 3 halogen, $C_1$-$C_6$ alkyl, $C_{6-10}$ aryl, or $C_2$-$C_6$ alkenyl substituents, preferably 1 or 2 substituents selected from halogen or $C_1$-$C_3$ alkyl. In some embodiments, the cyclic diether is 1,4-dioxane.

Suitable linear diethers include a linear diether of the formula A-O-B-O-C wherein A, B, and C are the same or different, and are a $C_1$-$C_6$ alkyl, $C_{6-10}$ aryl, or $C_2$-$C_6$ alkenyl, each of which can be optionally substituted with one or more halogens. In some embodiments, A, B, and C are the same or different, and are a $C_1$-$C_3$ alkyl, phenyl, or $C_2$-$C_4$ alkenyl, each of which can be optionally substituted with one or more halogen. The linear diether can be a symmetrical or unsymmetrical diether of the formula $(C_nH_{2n+1})O(C_nH_{2n})O(C_nH_{2n+1})$ wherein for each moiety n is the same or different, and is 1 to 4, or is 1 to 2.

Suitable polyethers include, but are not limited to, dioxane and ethers based on polyalcohols, e.g., glycols or glycerols, e.g., ethylene glycol. In some embodiments, the ether is a dioxane, which can be 1,4-dioxane. Ethers based on glycol include, but are not limited to, 1,2-dimethyl ethylene glycol ether (1,2-DME or DME), diethyl ethylene glycol ether, dipropyl ethylene glycol ether, dibutyl ethylene glycol ether, methyl ethyl ethylene glycol ether, methyl propyl ethylene glycol ether, methyl butyl ethylene glycol ether, ethyl propyl ethylene glycol ether, ethyl butyl ethylene glycol ether, and propyl butyl ethylene glycol ether.

In some embodiments, the modifier is an anhydride, for example an anhydride of the formula DOC(O)OC(O)E containing 4 to 16 carbon atoms. Substituents D and E of the anyhydrides can be the same or different, and can be alkyl, cycloalkyl, cycloalkylene (wherein D and E are joined and the anhydride moiety is a ring member), aryl, or other groups having a total of 16 carbon atoms, for example $C_1$-$C_6$ alkyl, $C_3$-$C_6$ cycloalkyl, $C_3$-$C_6$ cycloalkylene, $C_{6-10}$ aryl; or $C_2$-$C_6$ alkenyl groups optionally substituted with 1, 2, or 3 substituents selected from halogen, cyano, nitro, $C_1$-$C_3$ alkyl, phenyl, or $C_2$-$C_6$ alkenyl. Suitable alkylene groups can be ethylene and propylene, optionally substituted with a phenylene at two positions (e.g., phthalic anhydride), and suitable alkyl groups can be methyl, ethyl, propyl, n-butyl, iso-butyl, t-butyl, and other higher alkyl groups. In some embodiments, the anhydride is an acetic anhydride.

In some embodiments, the modifier is an amine, for example an amine of the formula $R^a{}_{3-a}NH_a$ wherein a can be 1 or 0, and each $R^a$ can be the same or different, and can be alkyl, cycloalkyl, cycloalkylene, aryl, or other groups having a total of 16 carbon atoms, for example $C_1$-$C_6$ alkyl, $C_3$-$C_6$ cycloalkyl, $C_3$-$C_6$ cycloalkyl, $C_3$-$C_6$ cycloalkylene, $C_{6-10}$ aryl, or $C_2$-$C_6$ alkenyl groups optionally substituted with 1, 2, or 3 substituents selected from halogen, cyano, nitro, $C_1$-$C_4$ alkoxy, phenyl, or $C_2$-$C_6$ alkenyl. Suitable alkyl groups can be methyl, ethyl, propyl, n-butyl, iso-butyl, or t-butyl, optionally further substituted with methoxy or ethoxy. Suitable amines include, but are not limited to, diethylamine and triethylamine, as well as amines such as pyrrolidine and quinuclidene.

In some embodiments, the modifier is an amide, for example an amide of the formula $R^b{}_{2-a}H_bNCR_a$ wherein b can be 1 or 0, $R^a$ is as defined above, and each $R^b$ can be the same or different, and can be alkyl, cycloalkyl, cycloalkylene, aryl, or other groups having a total of 16 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1, 2, or 3 substituents selected from halogen, cyano, nitro, $C_1$-$C_4$ alkoxy, $C_6$ phenyl, or $C_2$-$C_6$ alkenyl. Suitable alkyl groups can be methyl, ethyl, propyl, n-butyl, iso-butyl, or t-butyl, optionally further substituted with methoxy or ethoxy. The amide can be N,N-dimethylacetamide, or N-methylpyrrolidinone.

In some embodiments, the modifier is a silicate, which as used herein means an organic compound of the formula $Si(OR^c)_4$ wherein each $R^c$ can be the same or different, and can be alkyl, cycloalkyl, aryl, or other groups having a total of 10 carbon atoms, for example $C_1$-$C_6$ alkyl, $C_3$-$C_6$ cycloalkyl, $C_{6-10}$ aryl, or $C_2$-$C_6$ alkenyl groups optionally substituted with 1, 2, or 3 substituents selected from halogen, cyano, nitro, phenyl, or $C_2$-$C_6$ alkenyl. Suitable alkyl groups can be methyl, ethyl, propyl, n-butyl, iso-butyl, or t-butyl. The silicate can be tetraethylorthosilicate (also called tetraethoxysilane).

In some embodiments, the modifier is a silyl ether. The silyl ether can be of the formula $(R^aO)R_3Si$, wherein $R^a$ and each R is the same or different, and can be alkyl, cycloalkyl, aryl, or other groups having a total of 10 carbon atoms, for example $C_1$-$C_6$ alkyl, $C_3$-$C_6$ cycloalkyl, $C_{6-10}$ aryl, or $C_2$-$C_6$ alkenyl groups optionally substituted with 1, 2, or 3 substituents selected from halogen, cyano, nitro, phenyl, or $C_2$-$C_6$ alkenyl. Suitable alkyl groups can be methyl, ethyl, propyl, n-butyl, iso-butyl, or t-butyl. In an embodiment $R^a$ and each R is the same or different and is a $C_1$-$C_6$ alkyl or $C_6$ aryl group. Preferably, $R^a$ is a secondary or tertiary $C_3$-$C_{12}$ alkyl. The silyl ether can be, for example (trimethylsilyl)tert-butyl alcohol, more commonly known as tert-butoxytrimethylsilane.

In some embodiments, the modifier is a siloxane, for example a siloxane containing a total of 2 to 10 Si atoms, and substituted with alkyl, cycloalkyl, cycloalkylene, aryl, or other groups having a total of 10 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1 to 6 substituents selected from halogen, cyano, nitro, phenyl, or $C_2$-$C_6$ alkenyl. In an embodiment the siloxane is a linear or cyclic siloxane substituted with $C_1$-$C_8$ alkyl, halogenated $C_1$-$C_8$ alkyl, $C_6$ aryl, or halogenated $C_6$ aryl groups, optionally wherein at least one of the substituents is a secondary or tertiary $C_3$-$C_6$ alkyl. Suitable siloxanes include, but are not limited to, hexamethyldisiloxane and 1,3-bis-tert-butyl-1,1,3,3-tetramethyldisiloxane.

In some embodiments, the modifier is an ester. Suitable esters include, but are not limited to, secondary or tertiary $C_2$-$C_8$ alkyl esters of $C_1$-$C_8$ aliphatic or aromatic carboxylic acids, for example tert-butyl pivalate and tert-butyl acetate. Esters can also be cyclic lactones such as caprolactone.

In some embodiments, the modifier is a carbonate, for example a carbonate of the formula $R^aOC(=O)OR$ wherein each $R^a$ and R is the same or different, and is an alkyl, cycloalkyl, cycloalkylene, aryl, or other group having a total of 10 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1 to 6 substituents selected from halogen, cyano, nitro, phenyl, or $C_2$-$C_6$ alkenyl. Preferably, $R^a$ and R is a $C_1$-$C_8$ alkyl or $C_6$ aryl group, more preferably a secondary or tertiary $C_3$-$C_{12}$ alkyl. The carbonate can be di-tert-butyl carbonate.

In some embodiments, the modifier is a carbamate, for example a carbamate of the formula $R^aOC(=O)NRR$ wherein $R^a$ and each R is the same or different, and is an alkyl, cycloalkyl, cycloalkylene, aryl, or other group having a total of 10 carbon atoms, for example $C_1$-$C_6$ alkyl, $C_3$-$C_6$ cycloalkyl, $C_3$-$C_6$ cycloalkylene, $C_{6-10}$ aryl; or $C_2$-$C_6$ alkenyl groups optionally substituted with 1 to 6 substituents selected from halogen, cyano, nitro, phenyl, or $C_2$-$C_6$ alkenyl. Preferably, $R^a$ and each R is the same or different, and is a $C_1$-$C_8$ alkyl or $C_6$ aryl group. The carbamate can be methyl dimethylcarbamate or tert-butyl dimethylcarbamate.

In some embodiments, the modifier is a urea, for example a urea of the formula $R^aR^aN(=O)NRR$ wherein each $R^a$ and each R is the same or different, and is an alkyl, cycloalkyl, cycloalkylene, aryl, or other group having a total of 10 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1 to 6 substituents selected from halogen, cyano, nitro, phenyl, or $C_2$-$C_6$ alkenyl, preferably a $C_1$-$C_8$ alkyl, $C_3$-$C_8$ cycloalkylene, or $C_6$ aryl group. The urea can be 1,3-dimethyl-3,4,5,6-tetrahydro-2(1H)-pyrimidinone (DMPU).

In some embodiments, the modifier is a sulfoxide, for example a sulfoxide of the formula $R^aR^aS(=O)NRR$ wherein each $R^a$ and R is the same or different, and is an alkyl, cycloalkyl, cycloalkylene, aryl, or other group having a total of 10 carbon atoms, for example $C_1$-$C_6$ alkyl, $C_3$-$C_6$ cycloalkyl, $C_3$-$C_6$ cycloalkylene, $C_{6-10}$ aryl; or $C_2$-$C_6$ alkenyl groups optionally substituted with 1 to 6 substituents selected from halogen, cyano, nitro, phenyl, or $C_2$-$C_6$ alkenyl, preferably a $C_1$-$C_8$ alkyl or aryl group. The sulfoxide can be dimethylsulfoxide (DMSO).

In some embodiments, the modifier is a sulfone, for example a sulfone of the formula $R^aR^aS(=O)_2NRR$ wherein each $R^a$ and each R is the same or different, and is an alkyl, cycloalkyl, cycloalkylene, aryl, or other group having a total of 10 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1 to 6 substituents selected from halogen, cyano, nitro, phenyl, or $C_2$-$C_6$ alkenyl, preferably a $C_1$-$C_{12}$ alkyl, or aryl group, preferably a $C_1$-$C_8$ alkyl, $C_3$-$C_6$ cycloalkylene, or $C_6$ aryl group. The sulfone can be sulfolane.

In some embodiments, the modifier is a phosphoramide, for example a phosphoramide of the formula $P(=O)(NRR)(NR^aR^a)(NR^bR^b)$ wherein each $R^a$, $R^b$, and R is the same or different, and is an alkyl, cycloalkyl, cycloalkylene, aryl, or other group having a total of 10 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1 to 6 substituents selected from halogen, cyano, nitro, phenyl, or $C_2$-$C_6$ alkenyl, preferably a $C_1$-$C_{12}$ alkyl, $C_3$-$C_6$ cycloalkylene, or $C_6$ aryl group. The phosphoramide can be hexamethylphosphoramide.

In some embodiments, the modifier is a silane, which as used herein means an organic compound of the formula $HSi(OR^c)_3$ wherein each $R^c$ can be the same or different, and can be alkyl, cycloalkyl, cycloalkylene, aryl, or other groups having a total of 10 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1, 2, or 3 substituents selected from halogen, cyano, nitro, phenyl, or $C_2$-$C_6$ alkenyl. Suitable alkyl groups can be methyl, ethyl, propyl, n-butyl, iso-butyl, or t-butyl. The silane can be trimethoxysilane or triethoxysilane.

In some embodiments, the modifier is an acetal. Substituents of the acetals can be alkyl, cycloalkyl, cycloalkylene, aryl, or other groups having a total of 16 carbon atoms, for example $C_1$-$C_6$ alkyl, $C_3$-$C_6$ cycloalkyl, $C_3$-$C_6$ cycloalkylene, $C_{6-10}$ aryl, or $C_2$-$C_6$ alkenyl groups optionally substituted with 1, 2, or 3 substituents selected from halogen, cyano, nitro, $C_1$-$C_3$ alkyl, phenyl, or $C_2$-$C_6$ alkenyl. Suitable alkylene groups can be butylene and pentylene, and suitable alkyl groups can be methyl, ethyl, propyl, n-butyl, iso-butyl, t-butyl, and other higher alkyl groups. Suitable acetals include, but are not limited to, dimethoxymethane (DMM, formal, or methylal), diethoxymethane (DEM or ethylal), dibutoxymethane, or (DBM or butylal), and 1,3-dioxolane (dioxolane), In accordance with one example of the presently disclosed subject matter, the process includes treating an organoaluminum compound with a modifier that decreases the initial reducing strength of the organoaluminum compound. The molar ratio of the organoaluminum compound to the modifier can vary in a wide range, e.g., from about 0.1 to about 50. For example, the molar ratio of the organoaluminum compound to the reduction modifier can be from about 0.1 to about 1, from about 1 to about 5, from about 1 to about 10, from about 5 to about 10, from about 10 to about 20, from about 20 to about 30, from about 30 to about 40, or from about 40 to about 50. In some embodiments the molar ratio of the organoaluminum compound to the reduction modifier can be about 1:50, about 1:10, about 1:5, about 1:2, about 2:3, about 3:4, or about 4:5. Thus, the molar ratio of the organoaluminum compound to the modifier can vary from about 1:10 to about 4:5. In other embodiments the molar ratio of the organoaluminum compound to the reduction modifier can be from about 0.1:1 to about 50:1, for example, the molar ratio of the organoaluminum compound to the modifier can be from about 0.1:1 to about 1:1, from about 1:1 to about 5:1, from about 1:1 to about 10:1, from about 5:1 to about 10:1, from about 20:1 to about 30:1, from about 30:1 to about 40:1, or from about 40:1 to about 50:1. In still other embodiments, the molar ratio of the organoaluminum compound to the modifier can be about 1:10 to about 1:2, for example about 1:8 to about 1:3, or from about 1:6 to about 1:4. In an embodiment the molar ratio of the organoaluminum compound to the modifier is about 1:5.

The organoaluminum compound can coordinate to the modifier. Coordination of the organoaluminum compound and the modifier can be marked by evolution of heat, i.e., an exotherm. The coordination between the organoaluminum compound and the modifier can be performed at a temperature of about 0° C. or about 30° C. to about 150° C., or about 40° C. to about 120° C., and a pressure of from about 1 atm to about 250 atm.

The organoaluminum compound can be diluted in or mixed with the modifier for from about 1 minute to about 1 day. The process can further include cooling the mixture of the organoaluminum compound and the modifier to ambient conditions, e.g., a temperature of about 25° C. and a pressure of about 1 atm. At this point, a modified organoaluminum compound can be obtained.

In certain embodiments, the organoaluminum compound can be diluted in a solvent, which includes, but is not limited to, alkanes (including $C_2$-$C_{12}$ alkanes or $C_4$-$C_8$ alkanes, e.g., pentane, hexane, heptane, octane), aromatic hydrocarbons (benzene, toluene), and olefins or alkenes (including $C_2$-$C_{12}$ alkenes or $C_4$-$C_8$ alkenes, e.g., 1-butene, pentenes, hexenes). The organoaluminum compound can be diluted in a solvent before and/or after it is diluted in or mixed with the modifier. Alternatively, the organoaluminum compound can be used without diluting in a solvent before or after it is diluted in or mixed with modifier.

The modified organoaluminum compound can have properties that differ from the properties of unmodified organoaluminum compounds, e.g., lower initial reduction strength. The modified organoaluminum compound can be used as a co-catalyst for various catalytic processes. The modified organoaluminum compound can generally be used as a co-catalyst under the same reaction conditions as existing organoaluminum compounds. For example, a transition metal complex can be added to the modified organoaluminum compound in a standard ratio of organoaluminum to transition metal complex to produce a catalytic mixture. The organoaluminum compound activates the transition metal complex, which can be used for catalytic dimerization of ethylene, e.g., to produce 1-butene.

In certain embodiments, when the modified organoaluminum compound and the transition metal complex are combined to produce a catalytic mixture, the modifier can coordinate to or otherwise interact with transition metal species in the mixture, as well as coordinate to aluminum species. In this respect, in certain embodiments the modifier can modify both the organoaluminum compound and the transition metal complex. Accordingly, while the transition metal complex can be mixed separately with a catalyst modifier prior to adding the transition metal complex to the mixture of organoaluminum compound and the modifier, the presently disclosed subject matter does not require that the transition metal species be mixed with any catalyst modifier prior to adding the transition metal complex to the mixture of organoaluminum compound and the modifier.

The catalyst composition can be introduced to the reaction system as at least two or more components, which can be added sequentially. For example, the organoaluminum compound modified by a modifier (e.g., THF) and the transition metal complex diluted in a solvent (e.g., n-hexane) can be added to the reactor sequentially.

In some embodiments, the catalyst composition is prepared shortly before use. For example, the prepared catalyst composition is not stored for longer than 1 day, not longer than 1 hour, or not longer than 10 minutes before being employed in a catalytic process, e.g., catalytic dimerization of ethylene.

In some embodiments, the transition metal complex is not activated until shortly before being employed in a catalytic process, e.g., catalytic dimerization of ethylene. For example, the organoaluminum compound modified by a modifier is not brought into contact with the transition metal complex to activate the latter later than 30 minutes, not later than 15 minutes, not later than 5 minutes, not later than 3 minutes before the catalyst composition is employed.

By way of non-limiting example, the catalyst compositions can be used for catalytic dimerization of ethylene, e.g., to produce an α-olefin (e.g., 1-butene). Catalytic dimerization of ethylene can be carried out as a continuous reaction or a batch reaction. Catalytic dimerization of ethylene can proceed as a homogeneous reaction (e.g., in the liquid phase), or as a heterogeneous reaction. In some embodiments, catalytic dimerization of ethylene proceeds as a homogeneous liquid phase reaction.

Catalytic dimerization of ethylene can be performed at a temperature of from about 20° C. to about 150° C., from about 40° C. to about 100° C., from about 20° C. to about 70° C., from about 50° C. to about 70° C., from about 50° C. to about 55° C., or from about 55° C. to about 65° C. In some embodiments, catalytic dimerization of ethylene is performed at a temperature of about 60° C. Catalytic dimerization of ethylene can be performed at a pressure of from about 5 bars to about 50 bars, from about 10 bars to about 40 bars, or from about 15 bars to about 30 bars. Catalytic dimerization of ethylene can be conducted in a batch, a selected volume of the presently disclosed catalyst composition can be introduced into a reactor provided with usual stirring and cooling systems, and can be subjected therein to an ethylene pressure, which can be from about 22 bars to about 27 bars. In some embodiments, catalytic dimerization of ethylene using the presently disclosed catalyst composition is conducted at an ethylene pressure of about 23 bar. One of ordinary skill in the art can adjust the temperature, pressure and other conditions of the reaction in order to bring about favorable properties of the reaction, for example, in order to ensure that the reaction system is present as a homogeneous liquid phase. The reaction product (e.g., 1-butene) can be extracted by any methods which one of ordinary skill in the art would consider to be suitable in the context of the presently disclosed subject matter. Suitable methods of extraction include, but are not limited to, distillation, precipitation, crystallization, and membrane permeation.

Catalytic dimerization of ethylene performed using the presently disclosed catalyst compositions can have advantages over existing methods. For example, in certain embodiments of the presently disclosed subject matter, ethylene can be dimerized to 1-butene with a shortened induction period, extended lifetime of the catalyst composition, improved catalyst stability, improved selectivity for the desired product, reduced formation of polymer side products, reduced fouling, and overall improved catalyst activity. For example, certain existing commercial processes for dimerization of ethylene to produce 1-butene, e.g., the Alphabutol™ system, are characterized by long induction periods during which negligible amounts of ethylene are consumed. When existing commercial processes for dimerization of ethylene to produce 1-butene, e.g., the Alphabutol™ system, are used on plant scale, the induction periods can be many hours long. In certain embodiments of the presently disclosed subject matter, catalyst compositions including organoaluminum co-catalysts modified by a modifier can be characterized by shorter induction periods on lab scale and on plant scale, e.g., induction periods of less than 5 hours, less than 3 hours, less than 2 hours, less than 1 hour, less than 30 minutes, less than 15 minutes, less than 10 minutes, less than 5 minutes, less than 3 minutes, less than 2 minutes, or less than 1 minute.

The processes for modifying organoaluminum co-catalysts, making catalyst compositions, and performing various catalytic processes can be coupled to various further subsequent reactions in order to obtain downstream products. By way of non-limiting example, the process for catalytic dimerization of ethylene to produce 1-butene can be coupled to further subsequent reactions in order to obtain downstream products. Downstream products are those obtained from oligomerization reactions, polymerization reactions, hydrogenation reactions, halogenation reactions, and other chemical functionalization reactions. The chemical functionalization products can be aromatic or non-aromatic compounds, saturated or unsaturated compounds, ketones, aldehydes, esters, amides, amines, carboxylic acids, alcohols, etc. Monomeric downstream products can be chlorobutene, butadiene, butanol, and butanone. In certain embodiments, the downstream products are those obtained from polymerization reactions. Polymerization reactions can be mono-polymerization reactions or co-polymerization reactions. The polymerization product can be poly-butene. Co-polymers can include α-olefin (e.g., 1-butene) and one or more co-monomers including, but not limited to: ethylene, propene, pentene, styrene, acrylic acid, and vinyl chloride. In certain embodiments, the co-polymer is a co-polymer of ethylene and 1-butene. The ethylene monomers can be present in a larger wt. % than the 1-butene monomers in the co-polymer. For example, the weight ratio of ethylene monomers to 1-butene monomers can be from about 50:1 to about 5:1, from about 30:1 to about 10:1, or from about 25:1 to about 15:1. One or ordinary skill in the art can vary the ratio relating the mass of ethylene monomers and 1-butene monomers in order to tune the desired properties of polyethylene or polypropylene, such as crystallinity and elasticity.

In some embodiments of the process for preparing a downstream product, the product includes compounds with chain lengths in proportions determined by or approximating to the Anderson Schulz Flory distribution (see P. L. Spath and D. C. Dayton. "Preliminary Screening—Technical and Economic Assessment of Synthesis Gas to Fuels and Chemicals with Emphasis on the Potential for Biomass-Derived Syngas", NREL/TP510-34929, December, 2003, pp. 95).

In some embodiments, the downstream products are further connected to yield fatty acids, e.g., with chain lengths in proportions determined by or approximating to the Anderson Schulz Flory distribution.

In some embodiments, the downstream products are further processed, particularly in the case where the downstream product is a polymer, particularly when it is a polyethylene derivative. In one aspect of this embodiment, this further processing can involve formation of shaped objects such as plastic parts for electronic devices, automobile parts, such as bumpers, dashboards, or other body parts, furniture, or other parts or merchandise, or for packaging, such as plastic bags, film, or containers.

EXAMPLES

The following examples are merely illustrative of the presently disclosed subject matter and they should not be considered as limiting the scope of the presently disclosed subject matter in any way.

The following experiments were conducted in a 300 mL jacketed Parr autoclave reactor (Parr Modell 4566). The standard conditions were 23 bars ethylene pressure and 60° C. for 1 hour.

Commercial Alphabutol™ System

To perform an experiment with the commercial Alphabutol™ system, 1 mL of a catalytic solution including 45 vol. % THF and 55 vol % of TNBT was dissolved in 50 mL of n-hexane prepared in a glove box under a nitrogen atmosphere. Prior to use, 3.6 mL of 1M TEAL solution was added to activate TNBT. The activated catalyst composition was introduced to the reactor by vacuum suction. The reactor was then pressurized with ethylene from a 2-liter aluminum gas cylinder (ethylene supply) to reach the desired pressure (23 bars in most experiments). The reaction pressure was controlled using a backpressure regulator, while the ethylene consumption was measured using a balance onto which the gas cylinder was placed. The reactor was equipped with a thermocouple to measure the temperature inside the reactor. Temperature, pressure, and ethylene consumption data were recorded using a data acquisition system. Prior to the catalyst/solvent injection, the reactor was heated to 80° C. under vacuum for at least two hours in order to eliminate all traces of moisture. The temperature was controlled by a heating mantle/furnace and cooling coil refrigeration. After terminating the reaction by depressurization, the product was collected, hydrolyzed with deionized water, and analyzed by GC and/or GC/MS.

Total ethylene consumption was measured by weight difference of the attached ethylene storage cylinder. The induction period was determined by monitoring the pressure in the reactor or the flow rate of the feed to the reactor. Once the reaction starts, ethylene feed was consumed. In a batch reactor, onset of reaction was manifested as a drop in absolute pressure. The pressure remained roughly constant during the induction period and started to drop once the induction period is over. The induction period was the time spent at roughly constant pressure once the reactants (ethylene) and catalyst composition have been brought into contact and before the reaction started.

Figure 3:
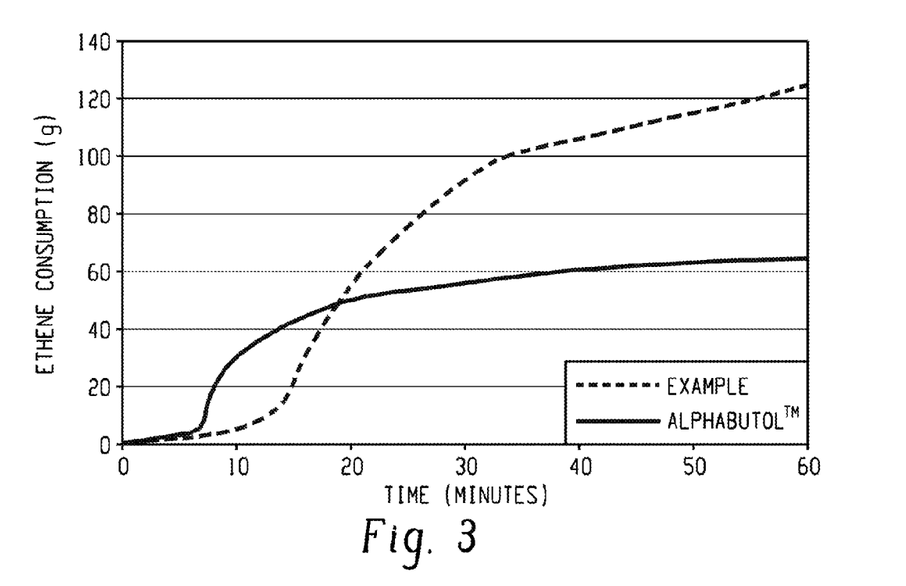
FIG. 3 represents the catalytic activity of the catalyst composition made by the process in accordance with one non-limiting example of the presently disclosed subject matter ("TAMED TEAL") as compared to the catalytic activity of the Alphabutol™ system.

The total ethylene consumption after 1 hour was about 63 g, and the induction period was about 8 minutes, as shown in FIG. 3. During the induction period, a negligible amount of ethylene (ethene) was consumed. In other lab-scale experiments with the Alphabutol™ system, an induction period was always observed, and the induction period was observed to vary up to about 15 minutes long. The catalyst composition of the Alphabutol™ system became inactive after approximately 30 minutes, as shown in FIG. 3.

Catalyst compositions including an organoaluminum co-catalyst (TEAL) modified by a modifier (THF, 1,4-dioxane, or 1,2-DME).

20 mmol of neat TEAL was diluted slowly in 100 mmol of a modifier: THF, 1,4-dioxane, or 1,2-DME for 15 minutes. The mixture was cooled down to ambient conditions before subsequent uses. 5 mL of TNBT was diluted in 10 mL of n-hexane to obtain a TNBT/n-hexane solution. 0.25 mL of the TNBT solution was mixed with 2.2 mL of the TEAL/modifier mixture prior to introduction into a batch reactor (e.g., an autoclave). The reactions were performed in the same conditions as the commercial Alphabutol™ system presented above.

The total ethylene consumption after 1 hour for the catalyst composition including TEAL/THF and TNBT/n-hexane was about 124 g, as shown in FIG. 3 (results with the modified catalyst system are shown as "Example"). The induction period for the catalyst composition including TEAL/THF and TNBT/n-hexane was shorter than that for the Alphabutol™ system, as ethylene consumption began immediately (albeit at a relatively low level). After about 15 minutes, ethylene consumption occurred at a faster rate, as shown in FIG. 3. The catalyst composition remained active throughout the experiment (1 hour) rather than becoming inactive. Repeat experiments came to similar results, e.g., the total ethylene consumption over 1 hour was about 93 g, and about 101 g, and the induction period was about 2 minutes. These results show that the catalyst lifetime, catalytic activity, and total ethylene consumption are greater when a catalyst composition including an organoaluminum co-catalyst (TEAL) modified by a modifier (THF) are used, as compared to the Alphabutol™ system.

The invention is further illustrated by the following non-limiting embodiments.

Embodiment 1

A process of making a catalyst composition, comprising: treating an organoaluminum compound with a modifier that decreases the initial reducing strength of the organoaluminum compound, wherein the modifier is selected from the group consisting of ethers, anhydrides, amines, amides, silicates, silyl ethers, siloxanes, esters, carbonates, carbamates, ureas, sulfoxides, sulfones, phosphoramides, silanes, and acetals; adding a transition metal complex to the mixture of the organoaluminum compound and the modifier; and obtaining a catalyst composition comprising the organoaluminum compound and the transition metal complex.

Embodiment 2

The process of embodiment 1, wherein the transition metal complex comprises at least one of the metals of Groups IV-B, V-B, VI-B, and VIII of the Periodic Table, preferably wherein the metal is titanium, zirconium, hafnium, vanadium, niobium, tantalum, chromium, molybdenum, tungsten, iron, cobalt, nickel, or a combination thereof, more preferably wherein the transition metal complex is titanium tetra-n-butoxide.

Embodiment 3

The process of any one or more of embodiments 1 to 2, wherein the organoaluminum compound is triethylaluminum.

Embodiment 4

The process of any one or more of embodiments 1 to 3, wherein the modifier a monoether, preferably tetrahydrofuran, or wherein the ether is a diether, preferably dimethyl ethylene glycol ether or 1,4-dioxane.

Embodiment 5

The process of any one or more of embodiments 1 to 4, wherein the transition metal complex is not mixed with a catalyst modifier prior to adding the transition metal complex to the mixture of the organoaluminum compound and the modifier.

Embodiment 6

The process of any one or more of embodiments 1 to 5, wherein the transition metal complex is diluted in a solvent, wherein the solvent is an alkane, aromatic hydrocarbon, olefin, or combination thereof.

Embodiment 7

The process of any one or more of embodiments 1 to 6, wherein the molar ratio of the organoaluminum compound to the modifier is about 1:10 to about 1:2, preferably about 1:5.

Embodiment 8

The process of any one or more of embodiments 1 to 7, wherein the catalyst composition is suitable for catalytic dimerization of ethylene, preferably wherein the catalyst composition is suitable for producing 1-butene.

Embodiment 9

The process of any one or more of embodiments 1 to 8, further comprising cooling the mixture of the organoaluminum compound and the modifier to ambient conditions prior to adding the transition metal complex to the mixture.

Embodiment 10

A catalyst composition for catalytic dimerization of ethylene made by the process of any one or more of embodiments 1 to 9.

Embodiment 11

A process for preparing an α-olefin, comprising: contacting an alkene with the catalyst composition of embodiment 10 to obtain the α-olefin, preferably wherein the α-olefin is 1-butene.

Embodiment 12

A process for preparing a polymer, comprising: contacting an alkene with the catalyst composition of embodiment 10 to obtain the polymer, preferably wherein the alkene is ethylene.

Embodiment 13

The process of embodiment 11 or 12, wherein the alkene and the catalyst composition come into contact in a homogeneous liquid phase.

Embodiment 14

The process of embodiment 13, wherein the alkene and the catalyst composition come into contact in a homogeneous liquid phase comprising at least about 50 wt. % 1-butene, based on the total weight of the homogeneous liquid phase.

Embodiment 15

The process of any one or more of embodiments 11 to 13, wherein the process is conducted at a pressure of from about 1 bars to about 250 bars, and a temperature of from about 30° C. to about 150° C.

Embodiment 16

A process for preparing a downstream product, comprising: preparing an α-olefin by the process of embodiment 11 or 13 or 14; and reacting the α-olefin to obtain the downstream product.

Embodiment 17

The process of embodiment 16, wherein the downstream product is a polymer.

Embodiment 18

The process of embodiment 17, wherein the polymer is a poly-α-olefin or copolymer comprising at least an α-olefin as a co-monomer.

Embodiment 19

The process of embodiment 18, wherein the downstream product is converted into a shaped body.

Embodiment 20

A process of making a catalyst composition for the dimerization of ethylene, comprising: treating an organoaluminum compound, preferably triethyl aluminum with a modifier that decreases the initial reducing strength of the organoaluminum compound, wherein the modifier is an ether, in particular tetrahydrofuran, dimethyl ethylene glycol ether or 1,4-dioxane ethers, and the molar ratio of the organoaluminum compound to the modifier is about 1:10 to about 1:2 or about 1:8 to about 1:3; adding to the mixture of the organoaluminum compound and the modifier a metal complex wherein the metal is titanium, zirconium, hafnium, vanadium, niobium, tantalum, chromium, molybdenum, tungsten, iron, cobalt, nickel, or a combination thereof, preferably titanium tetra-n-butoxide, optionally wherein the transition metal complex is not mixed with a catalyst modifier prior to adding the transition metal complex to the mixture of the organoaluminum compound and the modifier; and obtaining a catalyst composition comprising the organoaluminum compound and the metal complex. In this embodiment, the transition metal complex is diluted in a solvent, wherein the solvent is an alkane, aromatic hydrocarbon, olefin, or combination thereof.

Embodiment 21

A process for preparing 1-butene, comprising: contacting ethylene with the catalyst composition of embodiment 20 in a homogeneous liquid phase to obtain the 1-butene, preferably wherein the process is conducted at a pressure of from about 1 bars to about 250 bars, and a temperature of from about 30° C. to about 150° C.

Embodiment 22

A process for preparing a polymer, comprising: preparing an α-olefin by the process of embodiment 21; and reacting the 1-butene to obtain the polymer, wherein the polymer is a poly-1-butene or copolymer comprising units derived from 1-butene. Optionally, the polymer is shaped to form an article.

The term "about" or "substantially" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, or up to 1% of a given value. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. The singular forms "a", "an", and "the" include plural referents unless the context clearly dictates otherwise. "Or" means "and/or". Unless defined otherwise, technical and scientific terms used herein have the same meaning as is commonly understood by one of skill in the art to which this invention belongs.

All publications, patents, and patent applications cited herein are hereby expressly incorporated by reference for all purposes to the same extent as if each was so individually denoted.

Although the presently disclosed subject matter and its advantages have been described in detail, it should be understood that various changes, substitutions, and alterations can be made herein without departing from the spirit and scope of the presently disclosed subject matter as defined by the appended claims. Moreover, the scope of the presently disclosed subject matter is not intended to be limited to the particular embodiments described in the specification. Accordingly, the appended claims are intended to include within their scope such modifications.

What is claimed is:

1. A process of making a catalyst composition, comprising:
   treating an organoaluminum compound with a modifier that decreases the initial reducing strength of the organoaluminum compound, wherein the modifier is selected from the group consisting of ethers, anhydrides, amines, amides, silicates, silyl ethers, siloxanes, esters, carbonates, ureas, carbamates, sulfoxides, sulfones, phosphoramides, silanes, and acetals;
   adding a transition metal complex to the mixture of the organoaluminum compound and the modifier; and
   obtaining a catalyst composition comprising the organoaluminum compound and the transition metal complex;
   wherein the molar ratio of the organoaluminum compound to the modifier is about 1:10 to about 1:2.

2. The process of claim 1, wherein the transition metal complex comprises at least one of the metals of Groups IV-B, V-B, VI-B, and VIII of the Periodic Table.

3. The process of claim 1, wherein the organoaluminum compound is triethylaluminum.

4. The process of claim 1, wherein the modifier is a monoether, or wherein the ether is a diether.

5. The process of claim 1, wherein the transition metal complex is not mixed with a catalyst modifier prior to adding the transition metal complex to the mixture of the organoaluminum compound and the modifier.

6. The process of claim 1, wherein the transition metal complex is diluted in a solvent, wherein the solvent is an alkane, aromatic hydrocarbon, olefin, or combination thereof.

7. The process of claim 1, wherein the catalyst composition is suitable for catalytic dimerization of ethylene.

8. The process of claim 1, further comprising cooling the mixture of the organoaluminum compound and the modifier to ambient conditions prior to adding the transition metal complex to the mixture.

9. A catalyst composition for catalytic dimerization of ethylene made by the process of claim 1.

10. A process for preparing an α-olefin, comprising:
    contacting an alkene with the catalyst composition of claim 9 to obtain the α-olefin.

11. The process of claim 10, wherein the alkene and the catalyst composition come into contact in a liquid phase comprising at least about 50 wt. % 1-butene, based on the total weight of the liquid phase.

12. The process of claim 10, wherein the process is conducted at a pressure of from about 1 bars to about 250 bars, and a temperature of from about 30° C. to about 150° C.

13. The process of claim 1, wherein the transition metal is titanium, zirconium, hafnium, vanadium, niobium, tantalum, chromium, molybdenum, tungsten, iron, cobalt, nickel, or a combination thereof, the modifier is tetrahydrofuran, dimethyl ethylene glycol ether, 1,4-dioxane, or a combination thereof.

14. The process of claim 1, wherein the transition metal complex is free from modifier.

15. The process of claim 1, wherein the transition metal complex is present in the composition in a concentration of about 0.0001 to about 0.1 mol/dm$^3$.

16. The process of claim 1, wherein the organoaluminum compound is trimethylaluminum.

17. The process of claim 6, wherein the solvent is n-hexane.

18. The process of claim 1, wherein the mixture is not stored for longer than one day before being employed in a catalytic process.

19. The process of claim 1, wherein the transition metal complex is added to the mixture of the organoaluminum compound and the modifier not later than 30 minutes before being employed in a catalytic process.

* * * * *

UNITED STATES PATENT AND TRADEMARK OFFICE
CERTIFICATE OF CORRECTION

PATENT NO. : 9,724,681 B2
APPLICATION NO. : 15/115711
DATED : August 8, 2017
INVENTOR(S) : Sebastiano Licciulli and Roland Schmidt Page 1 of 1

It is certified that error appears in the above-identified patent and that said Letters Patent is hereby corrected as shown below:

On the Title Page

Item (12), "Lucciulli et al." should read --Licciulli et al.--.

Item (72), the inventor whose name reads "Sebastiano Lucciulli" should read --Sebastiano Licciulli--.

Signed and Sealed this
Twenty-sixth Day of June, 2018

Andrei Iancu
*Director of the United States Patent and Trademark Office*